United States Patent [19]
Bimczok et al.

[11] Patent Number: 5,525,263
[45] Date of Patent: Jun. 11, 1996

[54] HAIR AND BODY CLEANING COMPOSITION

[75] Inventors: Rudolf Bimczok, Seeheim; Thomas Stiehm, Gross-Zimmern; Viola Grohe, Mühltal, all of Germany

[73] Assignee: Wella Aktiengesellschaft, Darmstadt, Germany

[21] Appl. No.: 256,478

[22] PCT Filed: Nov. 25, 1993

[86] PCT No.: PCT/EP93/03304

§ 371 Date: Jul. 8, 1994

§ 102(e) Date: Jul. 8, 1994

[87] PCT Pub. No.: WO94/16676

PCT Pub. Date: Aug. 4, 1994

[30] Foreign Application Priority Data

Jan. 26, 1993 [DE] Germany .................. 43 01 994.3

[51] Int. Cl.$^6$ ........................................ A61K 7/06
[52] U.S. Cl. .............. 252/551; 252/552; 252/174.21; 252/DIG. 5; 252/DIG. 13; 252/DIG. 14; 424/70.1; 424/70.13

[58] Field of Search .................. 252/551, 174.21, 252/557, DIG. 1, DIG. 14, DIG. 5, 545, 174.17; 424/70

[56] References Cited

U.S. PATENT DOCUMENTS 4,759,875  7/1988  Hart ........................... 252/551
5,015,414  4/1991  Kamesai et al. ............. 252/545

OTHER PUBLICATIONS

Abstract: C87–099177/14; "Liquid detergent comps. having, stable liquid phase"; J62048796.

Primary Examiner—Linda Skaling Therkorn
Assistant Examiner—Necholus Ogden
Attorney, Agent, or Firm—Michael J. Striker

[57] ABSTRACT

The present invention is a hair and body cleaning composition containing a combination of at least one predetermined nitrogen-free thickener and a surfactant mixture of alkyl ether sulfate, ethoxylated sulfosuccinic acid hemiester and alkyl ether carboxylate or alkali polyglycoside. The hair and body cleaning composition according to the invention is distinguished by excellent compatibility with skin.

11 Claims, No Drawings

HAIR AND BODY CLEANING COMPOSITION

BACKGROUND OF THE INVENTION

The subject of the present invention is a hair and body cleaning composition based on a combination of a mixture of certain surfactants with certain nitrogen-free thickeners which is distinguished in that it is tolerated particularly well by skin.

Hair and body cleaning compositions contain surfactants as the principle ingredient. These surfactants are subject to a number of requirements. On the one hand, these surfactants must have a good foam forming capacity and a good cleaning action. On the other hand, they must be well tolerated by the eyes, skin and mucous membranes and be biodegradable.

A number of attempts have already been made to provide hair and body cleaning compositions which possess a good cleaning action and which are also well tolerated by the skin.

None of the hair and body cleaning compositions made available to date have fully satisfied all of the requirements mentioned above.

SUMMARY OF THE INVENTION

Therefore, it is an object of the present invention to provide a hair and body cleaning composition in which a good cleaning action is combined with excellent compatibility with skin.

In this regard, an outstanding solution to this problem has now been found in a composition containing a combination of an alkyl ether sulfate and an ethoxylated sulfosuccinic acid hemiester, a third surfactant which is selected from alkyl ether carboxylates and alkyl polyglycosides, and a nitrogen-free thickener.

According to the present invention the hair and body cleaning composition contains (A) 1 to 28 percent by weight of at least one alkali metal salt or alkaline-earth metal salt of a $C_{10}$- to $C_{18}$-alkyl ether sulfate ethoxylated with 1 to 10 units of ethylene oxide, (B) 1 to 28 percent by weight of at least one ethoxylated sulfosuccinic acid hemiester conforming to the general formula

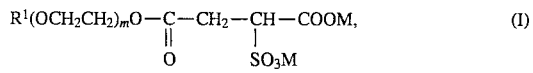

where $R^1$ represents a $C_{10}$- to $C_{18}$-alkyl group, M represents an alkali metal cation or alkaline-earth metal cation and m is a whole number from 1 to 10, (C) 1 to 28 percent by weight of at least one surfactant which is an alkyl ether carboxylate of the general formula

where $R^2$ represents a $C_{10}$- to $C_{18}$-alkyl group, M represents an alkali metal cation or alkaline-earth metal cation and n is a whole number from 1 to 20, and/or an alkyl polyglycoside of the general formula

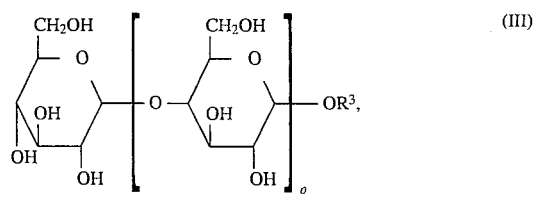

where $R^3$ represents a linear or branched, saturated or unsaturated $C_8$- to $C_{18}$-alkyl group, preferably a $C_{10}$-alkyl group, and o is a whole number from 1 to 5, preferably from 1 to 3, (D) 0.1 to 5 percent by weight of at least one nitrogen-free thickener ethoxylated methylglucose diesters of $C_{11}$- to $C_{20}$-fatty acids conforming to the general formula

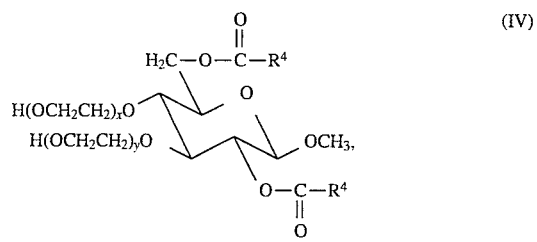

where $R^4$ is a $C_{11}$- to $C_{20}$-alkyl group, preferably a $C_{17}$-alkyl group, and the sum of x and y is 50 to 200, preferably 120, polyethylene glycol diesters of the general formula

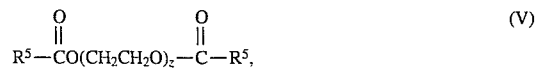

where $R^5$ represents a $C_{11}$- to $C_{20}$-alkyl group, preferably a $C_{17}$-alkyl group, and z is a whole number between 70 and 200, and/or mixtures of a) at least one polyethylene glycol ether of partial glycerides of fatty acid of the general formula

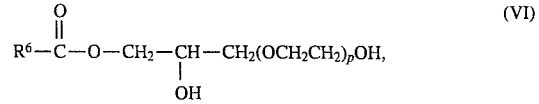

where $R^6$ is a $C_{11}$- to $C_{20}$-alkyl group and p is a whole number from 100 to 300 and b) at least one polyethylene glycol ether of a partial glyceride of fatty acid conforming to the general formula (VI), where $R^6$ is a $C_{11}$- to $C_{20}$-alkyl group and p is a whole number from 5 to 10, and the composition contains no additional surfactants other than components (A), (B) and (C).

In the present Application, alkyl group refers to linear, branched, saturated or unsaturated alkyl groups.

The hair and body cleaning composition according to the invention is clearly better tolerated by skin than known hair and body cleaning compositions while retaining comparable washing and cleaning characteristics.

The composition according to the invention preferably contains 4 to 10 percent by weight of component (A), 2 to 8 percent by weight of component (B) and 1 to 6 percent by weight of component (C). The weight ratio of component (A) to component (B) and component (A) to component (C) in the composition according to the invention is preferably 1:0.1 to 1:1. The weight ratio of component (A) to component (D) in the composition according to the invention is preferably 1:0.1 to 1:0.8.

The surfactant mixture of components (A), (B) and (C) is preferably contained in the composition according to the invention in quantities of 12 to 30 percent by weight.

The alkyl ether sulfate of component (A) is preferably ethoxylated with 5 units of ethylene oxide. The alkyl group of the alkyl ether sulfate preferably has 12 carbon atoms. The ethoxylated sulfosuccinic acid hemiester of component (B) is preferably ethoxylated with 3 units ethylene oxide. The alkyl group of the sulfosuccinic acid hemiester preferably has 12 carbon atoms.

The composition according to the invention preferably contains an alkyl ether carboxylate corresponding to general formula (II) as component (C). The alkyl ether carboxylate of component (C) is preferably ethoxylated with 10 units of ethylene oxide. The alkyl group of the alkyl ether carboxylate preferably has 12 carbon atoms. The alkyl ether carboxylate which can be contained in the composition according to the invention as component (C) is particularly preferably a lauryl alcohol polyethylene glycol ether carboxylate ethoxylated with 10 units ethylene oxide, for example, Marlinat® CM 105/80 available from Hüls AG, Marl, Germany.

The alkyl polyglycoside which can be contained in the composition according to the invention as component (C) is preferably decyl glycoside which is available, for example, in the form of a 55-percent aqueous solution from Seppic, Paris, France, as Oramix® NS 10.

The nitrogen-free thickeners contained in the composition according to the invention as component (D) are preferably mixtures composed of at least two polyethylene glycol ethers of partial glycerides of fatty acid a) and b) conforming to the general formula (VI).

The mixture of at least two polyethylene glycol ethers of partial glycerides of fatty acid a) and b) contained in tile composition according to the invention is preferably a mixture of a) polyethylene glycol ethers of monoglycerides and diglycerides of hydrogenated palm kernel oil ethoxylated with 200 units of ethylene oxide and b) the polyethylene glycol ethers of monoglycerides and diglycerides of coconut fatty acids ethoxylated with 7 units of ethylene oxide (CTFA adopted name: PEG-200 glyceryl hydrogenated palmitate and PEG-7 glyceryl cocoate), e.g. Rewoderm® LI S 80 sold by Rewo Chemische Werke GmbH, Steinau, Germany.

The methylglucose diester which can be contained in the composition according to the invention as component (D) is preferably methylglycoside dioleate ethoxylated with 120 units ethylene oxide, e.g. Glucamate® DOE-120 sold by Amerchol, Edison, U.S.A.

The polyethylene glycol diester of component (D) is preferably ethoxylated with 150 units ethylene oxide. The polyethylene glycol diester contained in the composition according to the invention as component (D) is preferably polyethylene glycol distearate ethoxylated with 150 units ethylene oxide, e.g. Rewopal PEG 6000 DS sold by Rewo Chemische GmbH, Steinau, Germany.

The water content in the composition according to the invention is preferably between 65 and 85 percent by weight. The pH of the composition according to the invention is preferably 4 to 7, more preferably 5 to 6, and the composition can be adjusted to tile desired pH, e.g., with citric acid, phosphoric acid or sodium hydroxide.

For the rest, the hair and body cleaning compositions described herein contain a mixture of the aforementioned components (A), (B), (C) and (D) with water and conventional ingredients used for cosmetic cleaning compositions. These compositions may take the form of clear or opaque solutions, emulsions or gels. The preferred preparation form is solution.

Examples of conventional ingredients for cosmetic cleaning compositions contained in the composition according to the invention are perfume oils in a quantity of approximately 0.5 to 5.0 percent by weight, opacifiers such as ethylene glycol distearate in quantities of approximately 0.5 to 5.0 percent by weight, pearlescing agents such as a mixture of fatty acid monoalkyloamide and ethylene glycol distearate in quantities of approximately 1.0 to 10.0 percent by weight, bactericides or fungicides such as 2,4,4-trichloro-2-hydroxydiphenyl ether or methylchloroisothiazolinone in quantities of approximately 0.01 to 1.0 percent by weight, hair and skin conditioning ingredients such as fatty acid esters, fatty alcohols, chitosan derivatives, tanolin derivatives and protein derivatives in quantities of 0.01 to 3 percent by weight, thinning agents such as 1,2-propylene glycol or ethoxylated sorbitan monolaurate in quantities of approximately 0.5 to 5.0 percent by weight, buffers such as sodium citrate or sodium phosphate in quantities of approximately 0.1 to 1.0 percent by weight, solubilizers such as ethoxylated and possibly hydrogenated castor oil in quantities of approximately 0.1 to 1.0 percent by weight, and dyestuffs such as fluorescein sodium salt in quantities of approximately 0.1 to 1.0 percent by weight.

The hair and body cleaning composition according to the invention preferably contains 2 to 20 percent by weight of cosmetic ingredients conventionally used in cosmetic cleaning compositions.

The subject matter of the present invention is explained more fully in the following examples.

Examples

Example 1:

mild hair and body cleaning composition

| | |
|---|---|
| 7.00 g | sodium lauryl ether sulfate ethoxylated with 1 to 4 units ethylene oxide |
| 4.20 g | disodium salt of the lauryl alcohol hemiester of sulfosuccinic acid ethoxylated with 1 to 4 units ethylene oxide |
| 1.00 g | lauryl alcohol polyethylene glycol ether carboxylate ethoxylated with 10 units ethylene oxide |
| 1.00 g | methylglycoside dioleate ethoxylated with 120 units ethylene oxide (Glucamate ® DOE-120, Amerchol, Edison, U.S.A.) |
| 2.00 g | lauryl dimethyl ammonium hydroxypropyl derivative of hydrolized collagen (Lamequat ® L, Henkel KGaA, Düsseldorf, Germany) |
| 0.60 g | triethylene glycol distearate |
| 0.20 g | lactic acid |
| 0.40 g | perfume oil |
| 83.60 g | water |
| 100.00 g | |

Example 2:

mild hair and body cleaning composition

| | |
|---|---|
| 7.00 g | sodium lauryl ether sulfate ethoxylated with 1 to 4 units ethylene oxide |
| 4.20 g | disodium salt of the lauryl alcohol hemiester of sulfosuccinic acid ethoxylated with 1 to 4 units ethylene oxide |
| 1.00 g | lauryl alcohol polyethylene glycol ether carboxylate ethoxylated with 10 units ethylene oxide |
| 2.00 g | mixture of polyethylene glycol ethers of monoglycerides and diglycerides of hydrogenated palm kernel oil ethoxylated with 200 units of ethylene oxide and polyethylene glycol ethers of monoglycerides and diglycerides of coconut fatty acid ethoxylated with 7 units of ethylene oxide (Rewoderm ® LI S 80, |

-continued

```
         Rewo Chem. Werke GmbH, Steinau, Germany)
  2.00 g lauryl dimethyl ammonium hydroxypropyl derivative
         of hydrolized collagen (Lamequat ® L, Henkel KGaA,
         Düsseldorf, Germany)
  0.60 g triethylene glycol distearate
  0.20 g lactic acid
  0.30 g perfume oil
 82.70 g water 100.00 g
```

Comparison tests for compatibility with skin

A test similar to the method described in P. J. Frosch, A. M. Kligman, The soap chamber test, *Am. Acad. Dermatol.* 1 (1979), pages 35 to 41, was conducted with 12 test subjects over a period of 5 days as a comparison test for skin compatibility of the composition according to the invention.

With respect to their compatibility with skin, Examples 3 and 4 according to the invention were compared with the hair and body cleaning compositions according to Examples I and II which are not the subject of the invention and do not contain nitrogen-free thickeners. The compositions of Examples 3 and 4, according to the invention, and Examples I and II which are not the subject of the present invention are shown in the following table.

TABLE 1

| Example | 3 | 4 | I | II |
|---|---|---|---|---|
| sodium lauryl ether sulfate ethoxylated with 1 to 4 units of ethylene oxide | 7.00g | 7.00g | 7.00g | 7.00g |
| disodium salt of the lauryl alcohol hemiester of sulfosuccinic acid ethoxylated with 1 to 4 units ethylene oxide | 4.20g | 4.20g | 4.20g | 4.20g |
| lauryl alcohol polyethylene glycol ether carboxylate ethoxylated with 10 units ethylene oxide | 2.80g | — | 2.80g | — |
| decyl glycoside (Oramix ® NS 10, Seppic, Paris, France) | — | 2.80g | — | 2.80g |
| mixture of polyethylene glycol ethers of monoglycerides and diglycerides of hydrogenated palm kernel oil ethoxylated with 200 units of ethylene oxide and polyethylene glycol ethers of monoglycerides and diglycerides of coconut fatty acid ethoxylated with 7 units of ethylene oxide (Rewoderm ® LI S 80, Rewo Chem. Werke GmbH, Steinau, Germany) | 2.00g | 2.00g | — | — |
| lauryl dimethyl ammonium hydroxypropyl derivative of collagen (Lamequat ® L, Henkel KGaA, Düsseldorf, Germany) | 2.00g | 2.00g | 2.00g | 2.00g |
| triethylene glycol distearate | 0.60g | 0.60g | 0.60g | 0.60g |
| lactic acid | 0.20g | 0.20g | 0.20g | 0.20g |

TABLE 1-continued

| Example | 3 | 4 | I | II |
|---|---|---|---|---|
| perfume oil | 0.30g | 0.30g | 0.30g | 0.30g |
| water | 80.90g | 80.90g | 82.90g | 82.90g |
|  | 100.00g | 100.00g | 100.00g | 100.00g |

The comparison test for skin compatibility was carried out with Finn chambers, aluminum chambers with a diameter of 12 min. A commercial filter paper with a diameter of 11 mm was first placed in the Finn chambers. One of the following aqueous test solutions (0.05 ml) was then applied to a filter paper.

The following test solutions were used:

(1) hair and body cleaning composition according to Example 3 in 8-percent aqueous solution (2) hair and body cleaning composition according to Example 4 in 8-percent aqueous solution (I) hair and body cleaning composition according to Example I in 8-percent aqueous solution, not the subject of the present invention (II) hair and body cleaning composition according to Example II in 8-percent aqueous solution, not the subject of the present invention (III) lauryl sulfate solution as standard solution in 0.2-percent aqueous solution A total of 5 Finn chambers—one chamber per test solution (1), (2), (I), (II) and (III)—were fastened to the underarm of 12 test subjects with commercial sticking plaster.

The Finn chambers remained in contact with the skin for 18 hours on the first test day. On the following four days, fresh test solutions were applied to the filter papers in the identical amounts and concentrations used on the first test clay. The Finn chambers remained in contact with the skin for 6 hours on days 2 to 5.

The reaction of the skin to the test solutions was first judged separately for development of erythema and fissures and for flaking according to the following grading system:

| erythema: | 0 negative |
| | 1 very slight spotty or diffuse erythema |
| | 2 easily recognizable, sharply delimited erythema |
| | 3 moderately severe erythema |
| flaking: | 0 negative |
| | 1 dryness |
| | 2 fine flaking |
| | 3 moderate flaking |
| | 4 severe flaking with large patches |
| fissures: | 0 negative |
| | 1 very superficial epidermal separation, fine cracks |
| | 2 more than one wide fissure |
| | 3 deep fissures with hemorrhaging or exudation |

In test solutions (I) and (II) corresponding to Examples I and II which are not the subject of the present invention there also occurred, in addition to flaking, slight erythema (less than 1) and superficial fissures (less than 1) which were not observed in test solutions 1 and 2 corresponding to Examples 3 and 4 according to the invention.

Since flaking occurred to a greater degree than erythema or fissures, only values for flaking were taken into account.

The absolute values for flaking obtained from both underarms of the twelve test subjects for the respective test solutions according to the grading system described above were compared to flaking produced by the standard solution (III) according to the following formula:

$$\text{relative flaking} = \frac{\text{flaking from test solution}}{\text{flaking from standard solution (III)}}$$

The numerical values shown in the following table 2 are averages for the values for relative flaking determined for the twelve test subjects according to the preceding formula.

TABLE 2

| test solution according to Example | 3 | 4 | I | II |
|---|---|---|---|---|
| relative flaking | 0.33 | 0.41 | 0.45 | 0.62 |

The relative values determined for flaking show that Examples 3 and 4 according to the invention are tolerated by the skin substantially better than are Examples I and II which are not the subject of the invention. In addition, in contrast to those portions of skin treated with the test solutions according to the examples which are not the subject of the invention, no erythema or fissures were established on the portions of skin treated in Examples 3 and 4 according to the invention.

Moreover, the comparison of the relative values for flaking of Examples 3 and 4 according to the invention with Examples I and II which are not the subject of the invention and are distinguished from Examples 3 and 4 according to the invention only by the absence of nitrogen-free thickeners clearly demonstrates the synergistic effect of the inventive combination of the surfactant mixture of components (A), (B) and (C) and the nitrogen-free thickeners of component (D) with respect to compatibility with skin.

The comparison test therefore shows that the hair and body cleaning compositions according to the invention are distinguished by excellent compatibility with skin.

All percentages indicated in the present Application represent percent by weight unless otherwise indicated.

It will be understood that each of the elements described above, or two or more together, may also find a useful application in other types of structures differing from the types described above.

While the invention has been illustrated and described as embodied in a hair and body cleaning composition, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. Hair and body cleaning composition containing
   from 1 to 28 percent by weight of at least one salt compound selected from the group consisting of alkali metal and alkaline-earth metal salts of a $C_{10}$- to $C_{18}$-alkyl ether sulfate ethoxylated with from 1 to 10 units of ethylene oxide,
   from 1 to 28 percent by weight of at least one ethoxylated sulfosuccinic acid hemiester of the formula $$R^1(OCH_2CH_2)_mO-CO-CH_2-CH(SO_3M)-COOM \qquad (I)$$

wherein $R^1$ is a $C_{10}$- to $C_{18}$-alkyl group, M is an alkali metal or alkaline-earth metal cation and m=a whole number from 1 to 10, from 1 to 28 percent by weight of at least one surfactant, wherein said at least one surfactant is selected from the group consisting of alkyl ether carboxylates of the formula $$R^2(OCH_2CH_2)_nOCH_2COOM' \qquad (II)$$

wherein $R^2$ is a $C_{10}$- to $C_{18}$-alkyl group, M' is an alkali metal or alkaline-earth metal cation and n=a whole number from 1 to 20, and alkyl polyglycosides of the formula $$\begin{array}{c}\text{CH}_2\text{OH} \\ \diagup\!\!-\!\!\text{O} \\ \text{OH} \\ \text{OH} \quad \text{OH}\end{array} \left[\begin{array}{c}\text{CH}_2\text{OH} \\ \diagup\!\!-\!\!\text{O} \\ -\text{O}-\text{OH} \\ \text{OH}\end{array}\right]_o -OR^3$$

wherein $R^3$ is a linear or branched, saturated or unsaturated $C_8$- to $C_{18}$-alkyl group and o is a whole number from 1 to 5, and from 0.1 to 5 percent by weight of at least one nitrogen-free thickener, said at least one nitrogen-free thickener being selected from the group consisting of ethoxylated methylglucose diesters of from $C_{11}$- to $C_{20}$-fatty acids according to the formula $$\begin{array}{c} H_2C-O-CO-R^4 \\ H(OCH_2CH_2)_xO \\ H(OCH_2CH_2)_yO \\ \end{array} \begin{array}{c} O \\ OCH_3 \\ OCO-R^4 \end{array} \qquad (IV)$$

wherein $R^4$ is a $C_{11}$- to $C_{20}$-alkyl group and a sum of x and y is from 50 to 200, polyethylene glycol diesters of the formula $$R^5-COO-(CH_2CH_2O)_z-CO-R^5 \qquad (V)$$

wherein $R^5$ is a $C_{11}$- to $C_{20}$-alkyl group and z is a whole number from 70 to 200, and mixtures of at least one polyethylene glycol ether of partial glycerides of fatty acids of the formula $$R^6-COO-CH_2-CHOH-CH_2(OCH_2CH_2)_pOH \qquad (VI)$$

wherein $R^6$ is a $C_{11}$- to $C_{20}$ alkyl group and p is a whole number form 100 to 300 and at least one polyethylene glycol ether of partial glycerides of fatty acids of the formula $$R^7-COO-CH_2-CHOH-CH_2(OCH_2CH_2)_{p'}OH \qquad (VI')$$

wherein $R^7$ is a $C_{11}$- to $C_{20}$ alkyl group and p' is a whole number from 5 to 10, and containing no additional surfactants other than said at least one surfactant, said at least one salt compound and said at least one ethoxylated sulfosuccinic acid hemiester.

2. Composition as defined in claim 1, containing from 4 to 10 percent by weight of said at least one salt compound.

3. Composition as defined in claim 1, containing from 2 to 8 percent by weight of said at least one ethoxylated sulfosuccinic acid hemiester.

4. Composition as defined in claim 1, containing from 1 to 6 percent by weight of said at least one surfactant.

5. Composition as define in claim 1, wherein said at least one salt compound and said at least one ethoxylated sulfosuccinic acid hemiester are present in a weight ratio of from 1:0.1 to 1:1 and said at least one salt compound and said at least one nitrogen-free thickener are present in a weight ratio of from 1:0.1 to 1:0.8.

6. Composition as defined in claim 1, containing from 12 to 30 percent by weight of a sum total of said at least one surfactant, said at least one salt compound and said at least one ethoxylated sulfosuccinic acid hemiester.

7. Composition as defined in claim 1, wherein said at least one surfactant includes one of said alkyl ether carboxylates.

8. Composition as defined in claim 1, containing at least two of said polyethylene glycol ethers of said partial glycerides of said fatty acids of the formula $$R^6\text{—COO—CH}_2\text{—CHOH—CH}_2(\text{OCH}_2\text{CH}_2)_p\text{OH} \qquad \text{(VI)}$$

wherein said $R^6$ is a $C_{11}$- to $C_{20}$ alkyl group and p is a whole number form 100 to 300 and at least two of said polyethylene glycol ethers of said partial glycerides of said fatty acids of the formula $$R^7\text{—COO—CH}_2\text{—CHOH—CH}_2(\text{OCH}_2\text{CH}_2)_{p'}\text{OH} \qquad \text{(VI')}$$

wherein said $R^7$ is a $C_{11}$- to $C_{20}$ alkyl group and p' is a whole number from 5 to 10.

9. Composition as defined in claim 1, further comprising from 65 to 85 percent by weight water.

10. Composition as defined in claim 1, further comprising 2 to 20 percent by weight of at least one conventional cosmetic ingredient.

11. Composition as defined in claim 10, wherein said at least one conventional cosmetic ingredient is selected from the group consisting of perfume oils, opacifiers, pearlescing agents, bactericides and fungicides, hair and skin conditioning ingredients, thinning agents, buffers, solubilizers and dyestuffs.

* * * * *